United States Patent [19]
Bryan

[11] Patent Number: 5,676,665
[45] Date of Patent: Oct. 14, 1997

[54] SPINAL FIXATION APPARATUS AND METHOD

[76] Inventor: Donald W. Bryan, 6151 S. Woodland Dr., Ogden, Utah 84403

[21] Appl. No.: 493,910

[22] Filed: Jun. 23, 1995

[51] Int. Cl.$^6$ .................................................. A61B 17/56
[52] U.S. Cl. .................................... 606/61; 606/73
[58] Field of Search ................................ 606/60, 61, 69, 606/70, 71, 72, 73

[56] References Cited

U.S. PATENT DOCUMENTS

| | | | |
|---|---|---|---|
| 4,524,765 | 6/1985 | De Zbikowski | 606/73 |
| 5,030,220 | 7/1991 | Howland | 606/61 |
| 5,074,864 | 12/1991 | Cozad et al. | 606/61 |
| 5,084,049 | 1/1992 | Asher et al. | 606/61 |
| 5,147,360 | 9/1992 | Dubousset | 606/72 |
| 5,334,203 | 8/1994 | Wagner | 606/61 |

Primary Examiner—Michael Powell Buiz
Assistant Examiner—Mark S. Leonardo
Attorney, Agent, or Firm—J. Winslow Young

[57] ABSTRACT

A spinal fixation apparatus and method for applying corrective forces to the spine through the use of one or more longitudinal rods placed adjacent the spine. A plurality of sublaminar hooks are configured to be independently mountable to the longitudinal rod and enable the surgeon to selectively engage portions of the spine against which the corrective forces are to be applied. Cross-link plates are provided and are used to interlink one longitudinal rod to another to provide a more rigid construct. The sublaminar hooks and the cross link plate system has a very low profile when secured to the spine. Side opening recesses in each sublaminar hook accommodate the lateral insertion of the longitudinal rod into the recess. A unique wedge bolt securely engages the longitudinal rod in the recess. The sublaminar hooks are oriented such that their wedge bolts face outwardly for ease of access for adjusting the same.

24 Claims, 4 Drawing Sheets

SPINAL FIXATION APPARATUS AND METHOD

BACKGROUND

1. Field of the Invention

This invention relates to a spinal fixation apparatus and, more particularly, to a unique, low-profile spinal fixation apparatus and method for securing the relative position of at least two vertebrae of the spine.

2. The Prior Art

Certain conditions of the spine such as scoliosis require the imposition of corrective forces on the spine in order to return the spine to its normal condition. These corrective forces must also be maintained on the spine while the spinal fusion is being completed. Other spinal conditions such as fractures require the secure fixation of the spine until healing and/or fusion has been achieved. Numerous devices have been disclosed for use in spinal correction and fixation and generally include one or more longitudinal rods placed generally parallel to the spinous process with various attachment systems interconnected between the longitudinal rods and selected components of the spine. These attachment systems include devices such as spinous process hooks, sublaminar hooks, pedicle screws, plates, and the like. Most of these devices are configured to securely engage the longitudinal rods and, as such, tend to be bulky in order to achieve the robust fixation of that particular device to the longitudinal rod. Further, each device is usually threaded on the longitudinal rod in series so that if the surgeon decides to add to or remove from the attachment system, a substantial portion of the attachment system must be disassembled and then reassembled serially in order to achieve the desired combination of devices in the attachment system.

In view of the foregoing it would be an advancement in the art to provide a unique attachment system for affixing the spatial relationship between the spine and the longitudinal rods. It would also be an advancement in the art to provide an attachment system having a low profile and that can be either attached or removed from the longitudinal rod individually in the absence of removal of any other devices. An even further advancement in the art would be to provide a cross-link mechanism for securing one longitudinal rod to another. Such a novel apparatus and method is disclosed and claimed herein.

BRIEF SUMMARY AND OBJECTS OF THE INVENTION

The present invention is a spinal fixation apparatus and method for use in supporting and/or imparting corrective forces to the spine. The apparatus includes at least one longitudinal rod for placement adjacent the spinous process along with two variations of sublaminar hooks for engaging the spine. Included also is a cross-link and clamp system for cross-linking a pair of longitudinal rods on each side of the spine. The sublaminar hooks along with some of the cross-link clamps are configured with a general C-shaped cross section to allow them to be affixed to the longitudinal rods from the side to eliminate the necessity of being threaded sequentially to the longitudinal rods. The sublaminar hooks include a unique wedging mechanism whereby the set screw employs a wedging action to securely anchor the longitudinal rod in the recess of the C-shaped cross section.

It is, therefore, a primary object of this invention to provide improvements in spinal fixation apparatus.

Another object of this invention is to provide improvements in the method of providing fixation of a spine.

Another object of this invention is to provide a sublaminar hook that can be mounted to a longitudinal rod from the side.

Another object of this invention is to provide a clamping mechanism for a clamping a sublaminar hook to the longitudinal rod by employing a wedging action of the set screw.

Another object of this invention is to provide a sublaminar hook having a reduced profile.

Another object of this invention is to provide a cross-link clamp that can be engaged to the longitudinal rod from the side.

Another object of this invention is to provide a cross-link plate having a reduced profile.

Another object of this invention is to provide an anchor for securing one end of the cross-link plate to the longitudinal rod.

These and other objects and features of the present invention will become more readily apparent from the following description and appended claims along with the accompanying drawing.

DETAILED DESCRIPTION OF THE PREFERRED EMBODIMENT

The invention is best understood by reference to the drawing wherein like parts are designated by like numerals throughout in conjunction with the following description.

General Discussion

The unique spinal fixation apparatus and method of this invention involves at least one longitudinal rod which can be surgically implanted adjacent and generally parallel to the spine. The longitudinal rod is interconnected to selected elements of the spine through the use of sublaminar hooks.

The sublaminar hooks are used to engage these elements of the spine and are then secured to the longitudinal rod at any preselected location along the length of the rod. Where necessary, forces may be imposed on the spine. These forces are imposed on the spine by engaging the spine with one or more sublaminar hooks which are then secured to the longitudinal rod at spaced locations. By engaging the spine with another one or more sublaminar hooks at spaced locations, the surgeon is able to impose corrective forces on the spine to create the corrective action on the spine. In this manner, the longitudinal rod can be used to impose a stretching force, a translational force, or even a compressive force on the spine. Further, the longitudinal rod can be prepared with a preselected contour so as to enable the surgeon to impart forces on the spine to bring the spine into conformation with the contour of the longitudinal rod. Advantageously, the sublaminar hook system of my invention allows the surgeon to engage any suitable portion of a vertebra and, also secure the sublaminar hook to the longitudinal rod. Thus, forces directed in several different directions can be simultaneously imposed on the spine by the simple expedient of determining the direction and degree of the various forces and then securing the sublaminar hooks to both the spine and the longitudinal rod to achieve these results.

The foregoing is readily achieved with my invention since the sublaminar hooks are configured to receive the longitudinal rod inserted therein laterally with the longitudinal rod then being securely wedged to the sublaminar hook by a wedge bolt that not only holds the longitudinal rod in place in the sublaminar hook but also can be tightened to essentially lock the sublaminar hook to the longitudinal rod.

The sublaminar hooks are configured with side-oriented openings so that they can be mounted easily to the longitudinal rod at any preselected location and in any predetermined sequence thus eliminating entirely the need to thread each hook onto the rod in a specific sequence. The sublaminar hooks are secured to the rod using the wedging action of the wedge bolt. Once clamped in this fashion the sublaminar hook is firmly engaged to the longitudinal rod. Importantly, fixation of the sublaminar hook is accomplished easily by simply tightening the wedge bolt. The sublaminar hook can be oriented through a full 360° circle around the longitudinal rod meaning that it can be used for either pushing or pulling against the particular element of the spine.

The foregoing wedging action of the longitudinal rod into the base of the side-oriented opening of the sublaminar hook also securely positions the sublaminar hook against the longitudinal rod to completely eliminate any tendency for the sublaminar hook to twist in any direction. Another advantage of my invention is that there is no tendency for the particular sublaminar hook to twist or turn as its clamp screw is being tightened thereby rendering my invention easier to assemble and affix to the spine. A further advantage to my invention is that it can be used not only to achieve fixation of the relative positions of spaced vertebrae, but it can also be used for altering the relative positions of the vertebrae. This latter feat is accomplished by securing one or more sublaminar hooks to both the longitudinal rod and the certain preselected vertebrae and then adjustably positioning the second preselected vertebrae and affixing the same to the longitudinal rod using the novel features of this invention as described hereinbefore.

A second longitudinal rod can be combined with the first longitudinal rod to achieve the desired fixation of the spine. In those instances a cross-link plate is used to securely interlink the two longitudinal rods. In this manner additional support, if necessary, can be supplied to the spine as determined by the surgeon.

Importantly, all of the components of my unique spinal fixation apparatus are designed to have a relatively low profile and thus render my invention highly desirable for use in those surgical procedures that could benefit from such a low profile. In addition to its low profile, the unique spinal fixation apparatus and method of this invention is convenient to use in that the sublaminar hooks and the cross-link plates can be secured to or removed from the longitudinal rods individually and at any preselected location without disturbing the other sublaminar hooks and cross-link plates. This feature allows the surgeon to modify the spinal fixation apparatus with ease and, more importantly, without disrupting the existing construct since all of the other sublaminar hooks and cross-link plates can be left in place while the changes are being made. In the event it is necessary to remove a sublaminar hook, the surgeon is readily able to simply move it laterally into disengagement from the longitudinal rod. This feature is a distinct advancement over the prior art wherein it was necessary to push the sublaminar hook downwardly toward the spinal cord thereby risking injury to the spinal cord.

Detailed Description

Figure 1:
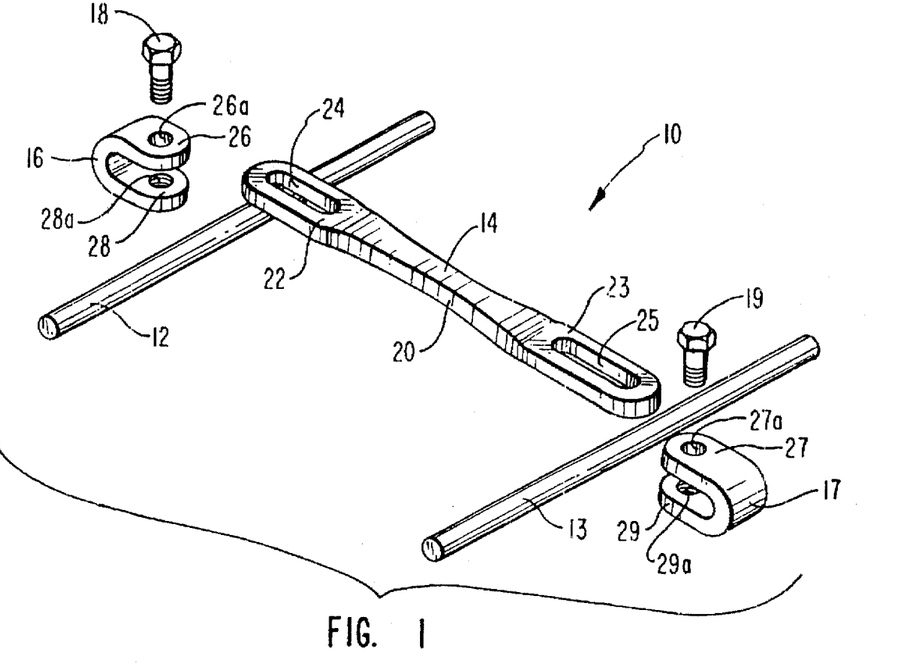
FIG. 1 is an exploded, perspective view of a pair of longitudinal rods and a cross-link plate along with a pair of C-clips for clamping the cross-link plate to the longitudinal rods.

Referring now to FIG. 1, the basal element of my spinal fixation apparatus is shown generally at 10 and includes a pair of longitudinal rods 12 and 13, a cross-link plate 14, and a pair of C-clips 16 and 17 with bolts 18 and 19 for securing cross-link plate 14 to longitudinal rods 12 and 13, respectively. Longitudinal rods 12 and 13 are conventional longitudinal rods suitable for spinal fixation and are commercially available in various standard sizes. Longitudinal rods 12 and 13 are fabricated from a surgical grade material such as stainless steel or titanium and are configured to be mounted along opposing sides of the spinous process (not shown). Longitudinal rods 12 and 13 may, where necessary, be bent or otherwise shaped by the surgeon to meet the surgical requirements of the spinal condition encountered during the surgical procedure.

Cross-link plate 14 is configured with a cross-bar 20 extending between a left eyelet 22 and a right eyelet 23 and serves to rigidly couple longitudinal rod 12 to longitudinal rod 13. In particular, left eyelet 22 is configured with an elongated slot 24 while right eyelet 23 is configured with an elongated slot 25 to provide the anchoring mechanism for anchoring cross-link plate 14 to longitudinal rods 12 and 13, respectively, by receiving therethrough bolts 18 and 19, respectively. Bolt 18 passes downwardly through elongated slot 24 into threaded engagement with C-clip 16 while bolt 19 passes downwardly through elongated slot 25 into threaded engagement with C-clip 17. C-clips 16 and 17, as their names imply, are configured with a C-shaped profile and are designed to receive the respective longitudinal rod 12 or 13 within the center of the C-shape in a close fitting relationship. C-clip 16 has an upper arm 26 and a lower arm 28 while C-clip 17 has an upper arm 27 and a lower arm 29. Each of upper arms 26 and 27 have holes 26a and 27a therethrough, respectively, while lower arms 28 and 29 have threaded throughbores 28a and 29a therethrough. Bolts 18 and 19 pass through holes 26a and 27a, respectively, to threadedly engage threaded throughbores 28a and 29a, respectively, thereby creating a clamping action for the respective C-clip, C-clips 16 and 17.

Figure 2:
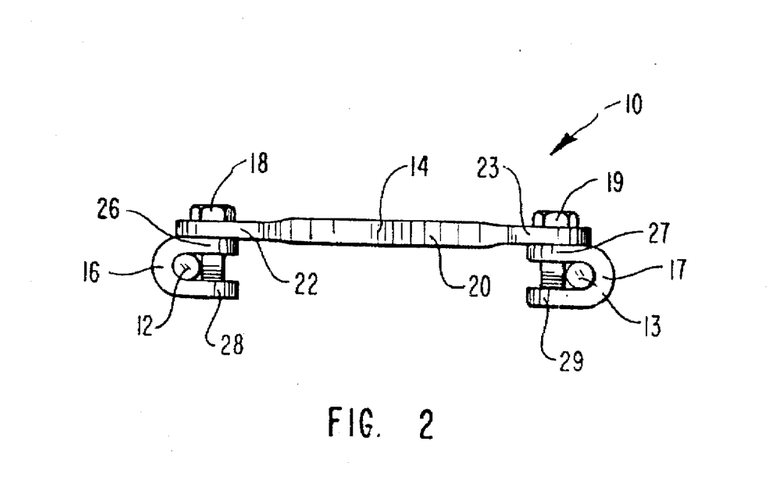
FIG. 2 is a side elevation of the cross-link plate of FIG. 1 mounted to the longitudinal rods by the C-clips.

Referring now also to FIG. 2, C-clip 16 is shown engaged about longitudinal rod 12 while C-clip 17 is shown engaged about longitudinal rod 13. C-clip 16 is placed over longitudinal rod 12 and eyelet 22 is mounted atop upper arm 26. Bolt 18 is then passed downwardly through elongated slot 24 and into threaded engagement with threaded throughbore 28a. Upon tightening of bolt 18, eyelet 22 is secured against upper arm 26 while C-clip 16 is securely anchored to longitudinal rod 12. Correspondingly, bolt 19 secures eyelet 23 to upper arm 23 while securely anchoring C-clip 17 to longitudinal rod 13. Advantageously, elongated slots 24 and 25 allow the surgeon to selectively adjust the spatial separation between longitudinal rods 12 and 13 through the simple expedient of selectively positioning the placement of bolts 18 and 19 therethrough thereby simultaneously positioning longitudinal rods 12 and 13 relative to each other as limited by the total range of adjustment provided by elongated slots 24 and 25. Further, if desired, cross-link plate 14 can be angularly offset relative to longitudinal rods 12 and 13 if necessary while enabling the surgeon to securely anchor the one to the other.

Figure 3:
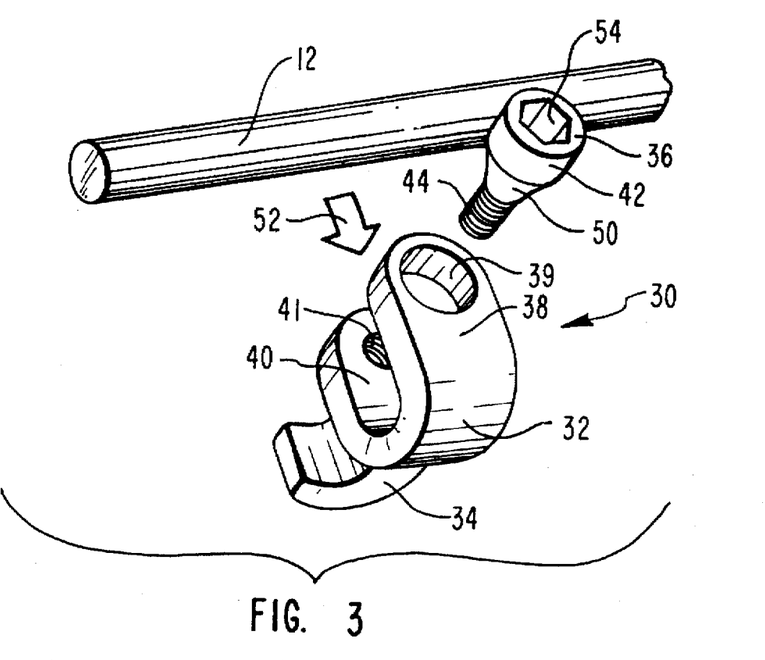
FIG. 3 is an exploded, perspective view of a first preferred embodiment of the unique sublaminar hook of this invention shown prior to having a longitudinal rod secured thereto.
Figure 4:
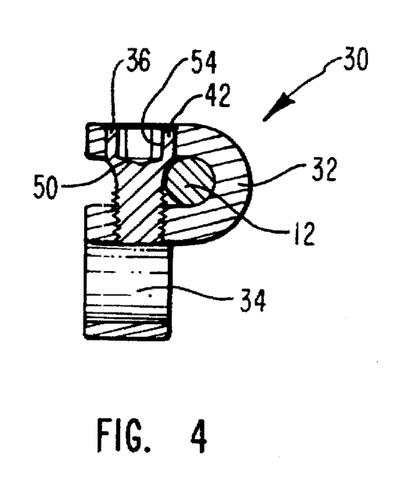
FIG. 4 is a cross-sectional view of the sublaminar hook of FIG. 3 mounted to the longitudinal rod and showing my unique wedging action for securely anchoring the sublaminar hook to the longitudinal rod.
Figure 5:
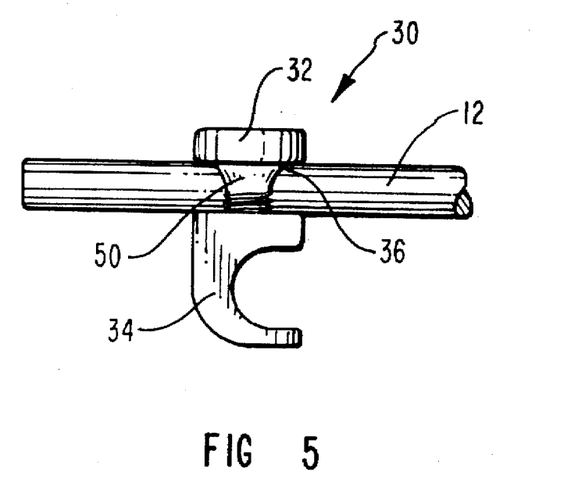
FIG. 5 is a side elevation of the sublaminar hook and longitudinal rod of FIG. 4.

Referring now to FIGS. 3–5, a first preferred embodiment of the unique sublaminar hook apparatus of my invention is shown generally at 30 and includes a C-shaped clamp body 32 having a downwardly oriented hook 34 and a wedge bolt 36. Sublaminar hook 30 is configured to be securely engaged to either of longitudinal rods 12 or 13, longitudinal rod 12 being shown herein for ease of illustration. Clamp body 32 includes an upper arm 38 and a lower arm 40 with an enlarged throughbore 39 formed in upper arm 38 and a threaded throughbore 41 formed axially in lower arm 40. Wedge bolt 36 is configured with a circumferentially enlarged head 42 which terminates downwardly in a threaded section 44 the threads of which are designed to threadedly engage the threads of threaded throughbore 41. Wedge bolt 36 includes a wedge shoulder 50 configured as a circumferential, tapered section extending between head 42 and threaded section 44. Wedge shoulder 50 has a slightly concave profile circumferentially the curvature of which approximates the external curvature of the surface of longitudinal rod 12. This curvature of wedge shoulder 50 provides a wedging action against longitudinal rod 12 as threaded section 44 of wedge bolt 36 is threadedly engaged in threaded throughbore 41 causing wedge bolt 36 to be pulled downwardly relative to clamp body 32. The upwardly increasing circumference of wedge shoulder 50 thereby exerts a very strong wedging action against longitudinal rod 12 to securely anchor longitudinal rod 12 against clamp body 32.

Sublaminar hook 30 readily enables the surgeon (not shown) to place hook 34 into engagement with the particular part of the spine (not shown) such as a sublaminae and then bring longitudinal rod 12 between upper arm 38 and lower arm 40 of clamp body 32 as shown schematically by arrow 52. Thereafter, wedge bolt 36 is engaged to clamp body 32 by being inserted downwardly through enlarged throughbore 39 and into threaded engagement with threaded throughbore 41. A socket 54 is formed in head 42 to receive therein a wrench (not shown) similar in operation to a conventional Allen wrench. Socket 54 allows the surgeon to impose a very strong wedging action against longitudinal rod 12 thereby securely engaging sublaminar hook 30 thereto. Another distinct advantage to sublaminar hook 30 is that it can be securely affixed at any preselected location along the length of longitudinal rod 30. Further, sublaminar hook 30 allows the surgeon to position sublaminar hook 30 on longitudinal rod 12 and thereafter force sublaminar hook 30 against the particular section of the spine engaged by hook 34 and then securely tighten wedge screw 36 to thereby hold the relative position between sublaminar hook 30 and longitudinal rod 12.

Clearly, of course, in order to be operable as described above, more than one sublaminar hook 30 must be used in order to allow the surgeon to impose the necessary corrective forces on the spine through the use of longitudinal rod 30. For example a first sublaminar hook 30 may be oriented on longitudinal rod 12 with hook 34 facing one direction while a second sublaminar hook 30 will be mounted to longitudinal rod 12 with hook 34 facing the opposite direction. By selectively positioning these sublaminar hooks 30 while creating a corrective force on longitudinal rod 12, the surgeon is readily able to apply the necessary corrective forces to the spine.

Figures 6, 7, 8:
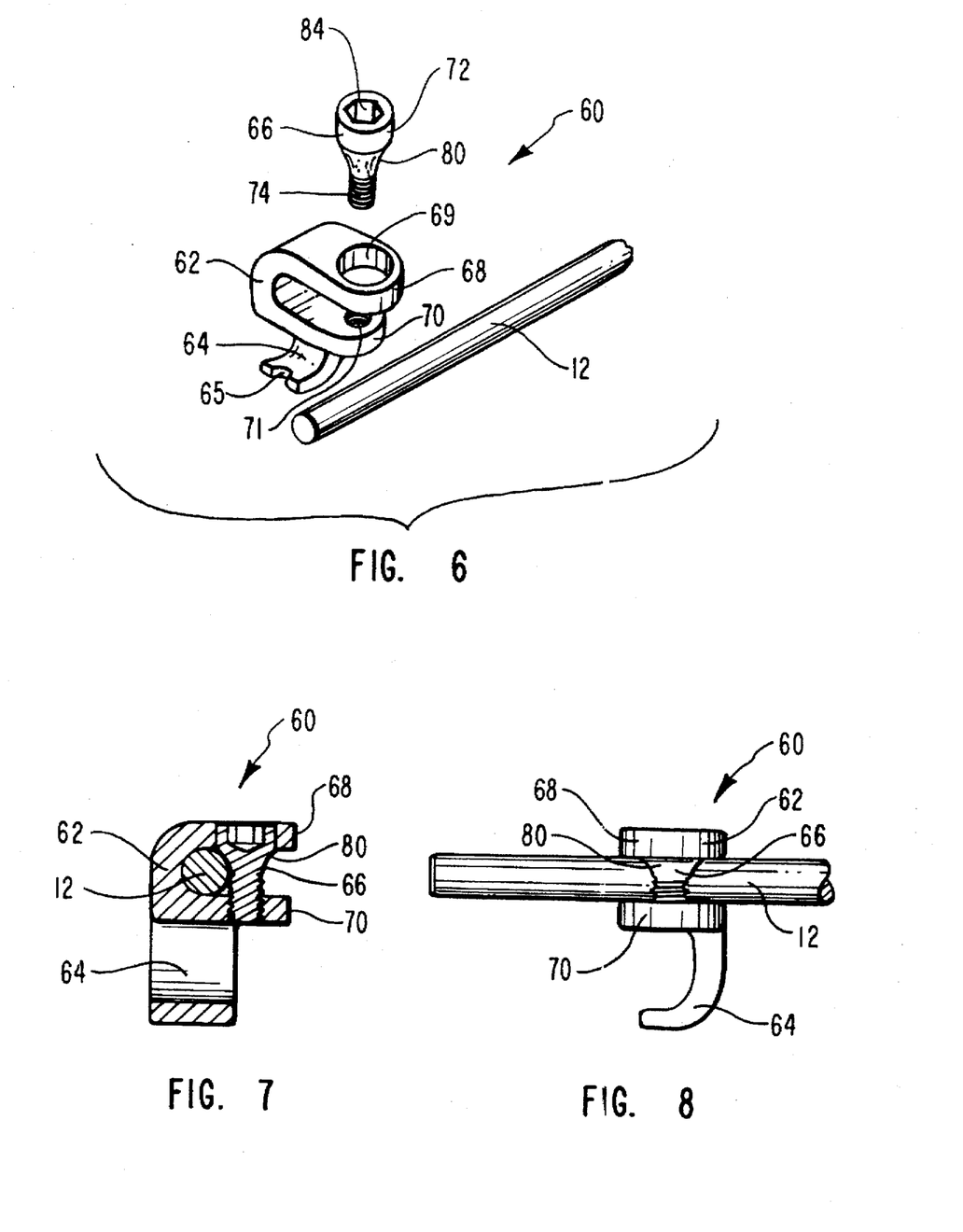
FIG. 6 is an exploded, perspective view of a second preferred embodiment of the unique sublaminar hook of this invention shown prior to being secured to a longitudinal rod.
FIG. 7 is a cross-sectional view of the sublaminar hook of FIG. 6 showing my unique wedging mechanism for securing the sublaminar hook to the longitudinal rod.
FIG. 8 is a side elevation of the sublaminar hook and longitudinal rod of FIG. 7.

Referring now to FIGS. 6–8, a second preferred embodiment of the sublaminar hook of this invention is shown generally at 60 and includes a C-shaped clamp body 62 having a downwardly oriented hook 64 and a wedge bolt 66. The leading edge of hook 64 includes a notch 65 which adapts sublaminar hook for use in engaging a pedicle, or the like. It should be noted that wedge bolt 66 is identical to wedge bolt 36 (FIGS. 3–6). Sublaminar hook 60 is configured to engage either of longitudinal rods 12 or 13 (FIGS. 1 and 2) although only longitudinal rod 12 is shown herein for ease of presentation. Clamp body 62 includes an upper arm 68 and a lower arm 70 with an enlarged throughbore 69 formed through upper arm 68 and a threaded throughbore 71 formed in lower arm 70 and in axial alignment with enlarged throughbore 69. Wedge bolt 66 is designed to be received into enlarged throughbore 69 and in threaded engagement in threaded throughbore 71 and, as such, has a circumferentially enlarged head 72 which dimensionally corresponds to enlarged throughbore 69. Wedge bolt 66 terminates distally in a threaded section 74, the threads of which match the threads of threaded throughbore 71. A wedge shoulder 80 is formed on wedge bolt 66 and is configured as a circumferentially tapered section having a slightly concave profile, the curvature of which generally approximates the external curvature of longitudinal rod 12. This feature allows the surgeon to slide longitudinal rod 12 laterally into the recess between upper arm 68 and lower arm 70 and securely wedge longitudinal rod 12 therein by inserting wedge bolt 66 into clamp body 62. Upon tightening wedge bolt 66 wedge shoulder 80 forcibly presses longitudinal rod against clamp body 62 thereby securely fastening sublaminar hook 60 to longitudinal rod 12. A socket 84 in enlarged head 72 allows the surgeon to engage wedge bolt 66 with a suitable wrench and thereby impose the desired degree of rotational force against wedge bolt 66 and, simultaneously, against longitudinal rod 12 and clamp body 62.

With specific reference to FIG. 7, it is readily seen that longitudinal rod 12 is positioned directly above hook 64 whereas sublaminar hook 30 (FIG. 4) holds longitudinal rod 12 at a slight offset above hook 34. Each of sublaminar hook 30 and sublaminar hook 60 provides the surgeon with the capability to selectively orient the desired sublaminar hook 30 or 60 along with longitudinal rods 12 and 13 in any number of preselected configurations in order to achieve the desired result on the spine.

Figure 9:
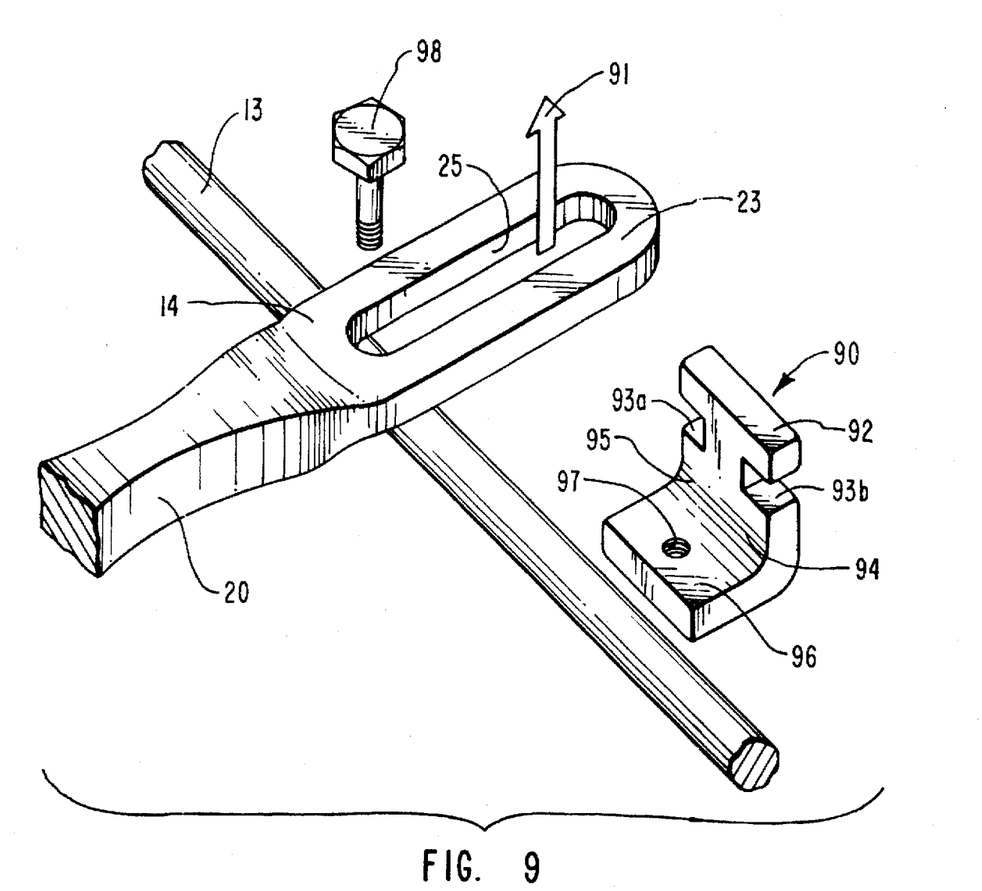
FIG. 9 is an exploded, perspective view of an anchor clip for mounting one end of the cross-link plate to the longitudinal rod.
Figure 10:
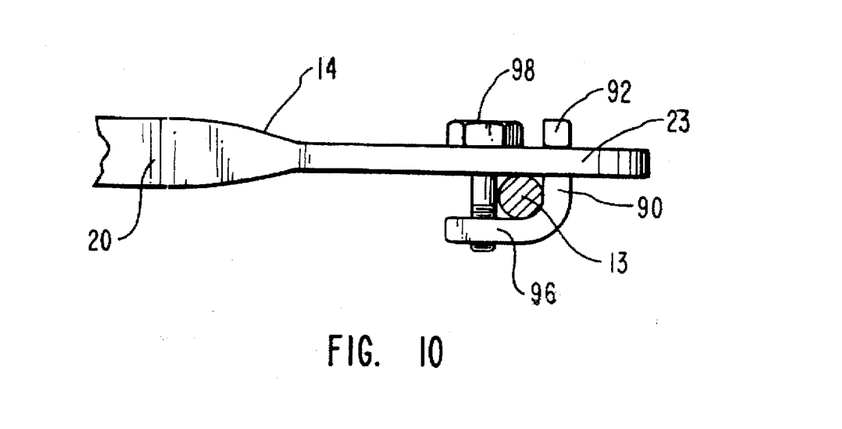
FIG. 10 is a side elevation of the cross-link plate of FIG. 9 secured to the longitudinal rod using my unique anchor clip.

Referring now to FIGS. 9 and 10, an anchor system for anchoring one end of cross-link plate 14 to longitudinal rod 13 is shown herein as an L-shaped anchor clip 90 which includes a cross arm 92, an upright 94, a base plate 96, and a bolt 98. A threaded bore 97 in base plate 96 is designed to engage bolt 98 in threaded relationship. Upright 94 includes a pair of notches 93a and 93b on opposing edges of upright 94 and help define cross arm 92. Notches 93a and 93b engage corresponding edges of eyelet 23 when upright 94 is oriented longitudinally with elongated slot 25 and then inserted upwardly into elongated slot 25 as illustrated schematically by arrow 91 before being rotated 90 degrees to bring notches 93a and 93b into engagement with eyelet 23. Cross arm 92 extends across the upper surface of eyelet 23 while upright 94 engages the lower surface of eyelet 23 to mount anchor clip 90 to eyelet 23.

The curvilinear intersection between upright 94 and base plate 96 is configured as a curved surface having a radius of curvature that conforms to the radius of curvature of longitudinal rod 13. This allows anchor clip 90 to securely engage longitudinal rod 13 to eyelet 23 when bolt 98 is engaged in threaded bore 97. One of the primary advantages of this system for anchoring eyelet 23 to longitudinal rod 13 over that of C-clip 17 (FIGS. 1 and 2) is that anchor clip 90 engages eyelet 23 directly to longitudinal rod 13 thereby reducing the total profile of the anchor system versus C-clip 17. This feature can be relatively important in certain surgical procedures where it is desired to keep the total profile of the spinal fixation system to a minimum.

The Method

The method of this invention is practiced by surgically preparing a preselected region of the spine to receive at least one longitudinal rod, longitudinal rod 12, although in most instances a second longitudinal rod, longitudinal rod 13, will also be used. At least two sublaminar hooks, sublaminar hooks 30 and 60, are then positioned to engage preselected portions of the underlying spine with their respective hooks, hooks 34 and 64. Sublaminar hooks 30 and 60 are each shown herein has having their respective hooks 34 and 64 oriented in opposite directions relative to their placement on longitudinal rod 12. However, it is to be clearly understood that hooks 34 and 64 can be oriented in either direction in order to accommodate right or left mounting to longitudinal rod 12 with hooks 34 and 64 being oriented either superiorly or inferiorly relative to the spine (not shown). This feature allows the surgeon complete flexibility in engaging the spine with sublaminar hooks 30 and 60 while engaging longitudinal rods 12 and 13 thereto. Advantageously, a plurality of sublaminar hooks 30 and 60 may be engaged to the spine at various locations with longitudinal rods 12 and 13 secured thereto in a snug, non-slip relationship. However, if desired, the surgeon is able to only partially tighten sublaminar hooks 30 and 60 on longitudinal rods 12 and 13 and then apply sufficient forces on sublaminar hooks 30 and 60 to move them into the desired positions prior to tightening the same. For example, it may be necessary for the surgeon to apply considerable corrective forces against the spine by moving sublaminar hook 30 relative to sublaminar hook 60 while keeping both slidingly secured to longitudinal rod 12. Thereafter, sublaminar hooks 30 and 60 are securely affixed to longitudinal rod 12. Further, preselected forces can be exerted on predetermined sectors of the spine through the selective engagement with sublaminar hooks 30 and 60 in combination with longitudinal rods 12 and 13. Additionally, the relative position between longitudinal rods 12 and 13 can be securely affixed through the use of C-clips 16 and 17 or anchor clip 90 and cross-link plate 14.

In summary, the apparatus and method of this invention provides the surgeon with a spinal support system that is highly adaptable for use in treating a variety of spinal conditions. Further, sublaminar hooks 30 and 60 effectively eliminate the need, in most instances, for the use of pedicle screws (not shown) or other screw-like devices (not shown) which require penetration of the bone structure of the spine. Instead, the surgeon simply engages the particular element of the spine with hooks 34 and 64 and then affixes the respective clamp body, clamp bodies 32 and 62 to the respective longitudinal rod, longitudinal rods 12 and 13. Cross-link plate 14 is then affixed between longitudinal rods 12 and 13 using either C-clips 16 and 17 or two anchor clips 90. Clearly, of course, a plurality of sublaminar hooks 30 and 60 can be used along with a plurality of cross-link plate 14 to achieve the desired construct for the spine. Advantageously, these various elements can be selectively added to and removed from longitudinal rods 12 and 13 without disturbing the remaining elements. Further, all of sublaminar hooks 30 and 60, C-clips 16 and 17, and anchor clip 90 in combination with longitudinal rods 12 and 13 provide a total construct that has a significantly low profile when implanted in a patient.

Another important feature of my invention is that the various elements such as C-clips 16 and 17, sublaminar hooks 30 and 60, and anchor clip 90 can each be tightened or loosened from the top surface. This means that the surgeon at all times has complete access to the tightening/loosening mechanisms for these components. Further, the surgeon is also able to partially tighten, for example, two sublaminar hooks 30 at spaced locations and then apply a distractor between the two sublaminar hooks 30 causing them to be moved apart to a predetermined configuration and then tightening the same to secure this new conformation of the spine. In other words, my invention is designed to avoid the problem associated with prior art devices that are designed around the "all or nothing" principle of engagement whereby they are either freely movable or securely locked. Accordingly, I am able to readily adjust or modify the placement and orientation of the various components of this invention and even replace the same without disturbing the other components.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A spinal fixation apparatus comprising:

a first longitudinal rod for implantation adjacent and generally parallel with the spinous processes of the spine;

a first sublaminar hook for engaging a portion of a first vertebra of the spine;

a first mounting means on said first sublaminar hook for adjustably mounting said first sublaminar hook to said first longitudinal rod at a first position, said first mounting means comprising a body having said first sublaminar hook extending therefrom, said body having an upper arm and a lower arm forming a C-shaped recess for receiving said first longitudinal rod, said body including a transverse throughbore orthogonally through said upper arm and said lower arm, said throughbore in said upper arm being diametrally enlarged while said throughbore in said lower arm includes a threaded throughbore, said first mounting means including a wedge bolt for forcing said first longitudinal rod into said C-shaped recess, said wedge bolt having an elongated body with a threaded section at a first end and a diametrally enlarge bolt head at a second end with a tapered shoulder section adjacent said bolt head, said tapered shoulder section forcing said first longitudinal rod into said C-shaped recess threaded engagement of said threaded section with said threaded throughbore;

a second sublaminar hook for engaging a portion of a second vertebra of the spine; and a second mounting means on said second sublaminar hook for adjustably mounting said second sublaminar hook to said first longitudinal rod at a second position, said second mounting means comprising a body having said second sublaminar hook extending therefrom, said body having an upper arm and a lower arm forming a C-shaped recess for receiving said first longitudinal rod, said body including a transverse throughbore orthogonally through said upper arm and said lower arm, said throughbore in said upper arm being diametrally enlarged while said throughbore in said lower arm includes a threaded throughbore, said second mounting means including a wedge bolt for forcing said first longitudinal rod into said C-shaped recess, said wedge bolt having an elongated body with a threaded section at a first end and a diametrally enlarged bolt head at a second end with a tapered shoulder section adjacent said bolt head, said tapered shoulder section forcing said first longitudinal rod into said C-shaped recess upon threaded engagement of said threaded section with said threaded throughbore.

2. The spinal fixation apparatus defined in claim 1 wherein said spinal fixation apparatus includes a second longitudinal rod and a plurality of cross-link plates for releasably securing said first longitudinal rod to said second longitudinal rod.

3. The spinal fixation apparatus defined in claim 2 wherein said cross-link plate includes a cross-bar having an eyelet at each end, each eyelet having an elongated slot therethrough for adjustably affixing said cross-link plate to said longitudinal rods.

4. The spinal fixation apparatus defined in claim 3 wherein said cross-link plate includes a C-clip for mounting said eyelet to said longitudinal rod.

5. A spinal fixation apparatus comprising:

a first longitudinal rod for implantation adjacent and generally parallel with the spinous processes of the spine;

a first sublaminar hook for engaging a portion of a first vertebra of the spine;

a first mounting means on said first sublaminar hook for adjustably mounting said first sublaminar hook to said first longitudinal rod at a first position;

a second sublaminar hook for engaging a portion of a second vertebra of the spine;

a second mounting means on said second sublaminar hook for adjustably mounting said second sublaminar hook to said first longitudinal rod at a second position; and a second longitudinal rod and a plurality of cross-link plates for releasably securing said first longitudinal rod to said second longitudinal rod, each of said cross-link plates including a cross-bar having an eyelet at each end, each eyelet having an elongated slot therethrough for adjustably affixing said cross-link plate to said longitudinal rods, said cross-link plate including an anchor clip for mounting said cross-link plate to said longitudinal rod, said anchor clip being configured with an L-shaped profile having a leg forming an upright, said upright having a cross-bar at a first end, said upright terminating in a foot formed as a base plate at a second end, said cross-bar being formed above opposing notches in said upright, said upright passing upwardly through said elongated slot in said eyelet with said notches engaging said eyelet when said upright is rotated across said eyelet, said anchor clip engaging said longitudinal rod in an angle formed between said leg and said foot of said L-shape when said base plate is secured to said eyelet, said anchor clip including a bolt means for securing said base plate to said eyelet thereby securing said longitudinal rod between said eyelet and said anchor clip.

6. A low profile apparatus for straightening and stabilization of the spine comprising:

a first longitudinal rod for placement adjacent the spinous process of the spine, said longitudinal rod having a cylindrical profile; and a plurality of sublaminar hooks mounted to said longitudinal rod, each of said sublaminar hooks having a side mounting means configured as a C-shaped recess for mounting said sublaminar hook to said longitudinal rod with said longitudinal rod being received in said C-shaped recess.

7. The low profile apparatus defined in claim 6 wherein said sublaminar hooks comprise a first sublaminar hook and a second sublaminar hook, said first sublaminar hook being adapted to be affixed to the spine at a first location and said second sublaminar hook being adapted to be affixed to the spine at a second location spaced from the first location.

8. The low profile apparatus defined in claim 6 wherein said side mounting means of each of said sublaminar hooks comprises a clamp body having a lateral slot, said slot having an opening and a base, said opening slidingly receiving said longitudinal rod, said base of said slot having a cylindrical profile corresponding to said cylindrical profile of said longitudinal rod, said clamp body including a wedge bolt transecting said slot, said wedge bolt having a lower threaded section for threaded engagement with said clamp body and an enlarged head with a wedge shoulder between said enlarged head and said lower threaded section, said wedge shoulder forcing said longitudinal rod into said base when said wedge bolt is threadedly tightened into said clamp body.

9. The low profile apparatus defined in claim 6 wherein said low profile apparatus includes a second longitudinal rod and at least one cross-link plate mounted between said first longitudinal rod and said second longitudinal rod.

10. The low profile apparatus defined in claim 9 wherein said cross-link plate includes a cross-bar with an eyelet at each end, each eyelet having an elongated slot.

11. A low profile apparatus for straightening and stabilization of the spine comprising:

a first longitudinal rod and a second longitudinal rod for placement adjacent the spinous process of the spine, each of said first longitudinal rod and said second longitudinal rod having a cylindrical profile;

at least one cross-link plate mounted between said first longitudinal rod and said second longitudinal rod, said cross-link plate including a cross-bar with an eyelet at each end, each eyelet having an elongated slot, said cross-link plate including clamp means for clamping said cross-link plate to said longitudinal rods, said clamp means including a C-clip formed into a C-shaped configuration having an upper arm and a lower arm with a recess between said upper arm and said lower arm, said recess being dimensionally configured to receive said longitudinal rods therein, said lower arm having a threaded throughbore and said upper arm having a bore therethrough in axial alignment with said threaded throughbore, said clamp means including a bolt, said bolt passing through said elongated slot and said bore and into threaded engagement in said threaded throughbore thereby securing said eyelet to said C-clip and said longitudinal rod in said recess in said C-clip; and a plurality of sublaminar hooks mounted to said longitudinal rods, each of said sublaminar hooks having a side mounting means for mounting said sublaminar hook to said longitudinal rod.

12. The low profile apparatus defined in claim 11 wherein said cross-link plate includes an anchor clip for anchoring said eyelet to said longitudinal rod, said anchor clip having an L-shaped profile with an upright having a pair of opposing notches at one end and a base plate at the other end, said notches engaging corresponding sides of said eyelet with said longitudinal rod engaged on said baseplate, said base plate including a threaded throughbore, said anchor clip including bolt means for passing through said elongated slot into threaded engagement with said threaded throughbore to securely affix said base plate to said eyelet thereby securing said longitudinal rod to said eyelet.

13. A spinal fixation apparatus comprising:

a longitudinal rod means for placement adjacent and generally parallel to the spinous process of the spine;

a plurality of hook members releasably affixed to said longitudinal rod means, said hook members having hooks, each of said hooks being configured to releasably engage preselected portions of the spine thereby affixing the spine to said longitudinal rod means; and mounting means on each of said hook members for mounting said hook member to said longitudinal rod means, said mounting means comprising a clamp body having a C-shaped recess for receiving said longitudinal rod therein, said clamp body including a wedge bolt for wedging said longitudinal rod in said C-shaped recess.

14. The spinal fixation apparatus defined in claim 13 wherein said longitudinal rod means comprises a first longitudinal rod for placement adjacent and generally parallel to the spinous process of the spine along a first side of the spinous process.

15. The spinal fixation apparatus defined in claim 14 wherein said longitudinal rod means comprises a second longitudinal rod spaced from and generally parallel to said first longitudinal rod, said second longitudinal rod being placed on a second side of the spinous process from said first longitudinal rod.

16. The spinal fixation apparatus defined in claim 15 wherein said longitudinal rod means comprises a plurality of cross-link plates interconnected between said first longitudinal rod and said second longitudinal rod, each of said cross-link plates having an eyelet at each end.

17. The spinal fixation apparatus defined in claim 13 wherein said hook members include a first sublaminar hook and a second sublaminar hook, said first sublaminar hook having a clamp body and a hook extending outwardly from said clamp body, said clamp body having a recess formed in one face, said recess being dimensionally configured to receive said longitudinal rod means therein, said recess being formed in said clamp body between an upper arm and a lower arm, said upper arm having an enlarged throughbore and said lower arm having a threaded bore in axial alignment with said enlarged throughbore, said first sublaminar hook including a wedge bolt having an enlarged head at a proximal end with a threaded section at a distal end and a wedge shoulder between said proximal end and said distal end, said wedge bolt threadedly engaging said threaded bore with said threaded section with said enlarged head received in said enlarged throughbore thereby wedging said longitudinal rod in said recess with said wedge shoulder.

18. A spinal fixation apparatus comprising:

a longitudinal rod means for placement adjacent and generally parallel to the spinous process of the spine, said longitudinal rod means comprising a first longitudinal rod for placement adjacent and generally parallel to the spinous process of the spine along a first side of the spinous process, said longitudinal rod means comprising a second longitudinal rod spaced from the generally parallel to said first longitudinal rod, said second longitudinal rod being placed on the other side of the spinous process from said first longitudinal rod, said longitudinal rod means comprising a plurality of cross-link plates interconnected between said first longitudinal rod and said second longitudinal rod, each of said cross-link plates having an eyelet at each end, said cross-link plate including clamp means for clamping said eyelets of said cross-link plate to said longitudinal rods, said clamp means including a C-clip formed into a C-shaped configuration having an upper arm and a lower arm with a recess between said upper arm and said lower arm, said recess being dimensionally configured to receive said longitudinal rod therein, said lower arm having a threaded bore and said upper arm having a throughbore therethrough in axial alignment with said threaded bore, said clamp means including a bolt, said bolt passing through said elongated slot and said throughbore and into threaded engagement in said threaded bore thereby securing said eyelet to said C-clip and said longitudinal rod in said recess in said C-clip; and a plurality of hook members releasably affixed to said longitudinal rod means, said hook members being configured to releasably engage preselected portions of the spine thereby affixing the spine to said longitudinal rod means.

19. A spinal fixation apparatus comprising:

a longitudinal rod means for placement adjacent and generally parallel to the spinous process of the spine, said longitudinal rod means comprising a first longitudinal rod for placement adjacent and generally parallel to the spinous process of the spine along a first side of the spinous process, said longitudinal rods comprising a second longitudinal rod spaced from the generally parallel to said first longitudinal rod, said second longitudinal rod being placed on the other side of the spinous process from said first longitudinal rod, said longitudinal rod means comprising a plurality of cross-link plates interconnected between said first longitudinal rod and said second longitudinal rod, each of said cross-link plates having an eyelet at each end, said cross-link plate including an anchor clip for anchoring said eyelet to said longitudinal rod, said anchor clip having an L-shaped configuration with a pair of opposed notches at one end and a base plate at the other end, said opposed notches engaging said eyelet with said longitudinal rod engaged by said base plate, said base plate including a threaded bore, said anchor clip including bolt means for passing through said elongated slot into threaded engagement with said threaded bore to securely affix said base plate to said eyelet thereby securing said longitudinal rod to said eyelet; and a plurality of hook members releasably affixed to said longitudinal rod means, said hook members being configured to releasably engage preselected portions of the spine thereby affixing the spine to said longitudinal rod means.

20. A method for applying at least one corrective force to a spine comprising the steps of:

obtaining at least one longitudinal rod and a plurality of sublaminar hooks;

providing each of said sublaminar hooks with a clamp body having a side opening recess for receiving therein said longitudinal rod and a wedge bolt for forcibly engaging said longitudinal rod in said recess, said wedge bolt accommodation mounting said sublaminar hook to said longitudinal rod;

placing said longitudinal rod adjacent the spine;

engaging a first portion of the spine with a first sublaminar hook;

securing said first sublaminar hook to said longitudinal rod;

engaging a second portion of the spine with a second sublaminar hook, said second portion of the spine being located at a distance from said first portion of the spine;

imposing a corrective force on said second sublaminar hook relative to said first sublaminar hook; and engaging said second sublaminar hook to said longitudinal rod while maintaining said corrective force thereby using said longitudinal rod for imposing said corrective force on said spine.

21. The method defined in claim 20 wherein said providing step includes providing a second longitudinal rod and said placing step includes placing said second longitudinal rod adjacent said spine and generally parallel to said first longitudinal rod.

22. The method defined in claim 21 wherein said placing step includes mounting at least one cross-link plate between said first longitudinal rod and said second longitudinal rod.

23. The method defined in claim 22 wherein said placing step includes engaging at least one third sublaminar hook to said second longitudinal rod.

24. The method defined in claim 20 wherein said imposing step includes partially tightening said first sublaminar hook on said first longitudinal rod and then forcibly moving said first sublaminar hook relative to said second sublaminar hook thereby imposing a corresponding force on the spine and thereafter securing said first sublaminar hook on said first longitudinal rod.

* * * * *